United States Patent
Patterson

(12) 
(10) Patent No.: US 8,578,589 B2
(45) Date of Patent: Nov. 12, 2013

(54) TUBING ATTACHMENT TOOL AND METHODS OF USING SAME

(75) Inventor: Frank V. Patterson, Exeter, NH (US)

(73) Assignee: CreatiVasc Medical, LLC, Greenville, SC (US)

( * ) Notice: Subject to any disclaimer, the term of this patent is extended or adjusted under 35 U.S.C. 154(b) by 968 days.

(21) Appl. No.: 12/580,435

(22) Filed: Oct. 16, 2009

(65) Prior Publication Data

US 2010/0095510 A1  Apr. 22, 2010

Related U.S. Application Data

(60) Provisional application No. 61/105,977, filed on Oct. 16, 2008.

(51) Int. Cl.
*B23Q 7/00* (2006.01)
*B21D 39/00* (2006.01)
*A61B 17/00* (2006.01)

(52) U.S. Cl.
USPC ............ 29/559; 29/268; 606/205; 606/207

(58) Field of Classification Search
USPC .............. 606/205, 206, 207, 208; 433/159; 29/268, 559
See application file for complete search history.

(56) References Cited

U.S. PATENT DOCUMENTS

| | | | |
|---|---|---|---|
| D233,839 S | 12/1974 | Royse | |
| 4,189,839 A | 2/1980 | Manuel | |
| 4,955,896 A | 9/1990 | Freeman | |
| 4,976,617 A | 12/1990 | Carchidi | |
| 5,391,181 A * | 2/1995 | Johnson et al. | 606/207 |
| 5,443,479 A | 8/1995 | Bressi, Jr. | |
| 5,562,447 A | 10/1996 | Moy et al. | |
| 5,624,454 A | 4/1997 | Palti et al. | |
| 6,425,901 B1 | 7/2002 | Zhu et al. | |

* cited by examiner

*Primary Examiner* — Jermie Cozart
(74) *Attorney, Agent, or Firm* — Dority & Manning, P.A.

(57) ABSTRACT

In general, the present disclosure is directed to a tubing attachment tool. The tubing attachment tool includes first and second frames pivotally joined to one another such that the first and second frames can pivot to an open position and a closed position. Each of the first and second frames have a first handle end and a second end distal to the first handle end with each second end including a tubing grasping element. Each tubing grasping element includes a first curved surface and a second curved surface. When the first and second frames are in a closed position the first curved surfaces of the tubing grasping elements are aligned adjacent to one another and the second curved surfaces of the tubing grasping elements are aligned adjacent to one another such that the first curved surfaces define a first opening capable of housing an open end of tubing for attachment and the second curved surfaces define a second opening capable of grasping a portion of tubing inserted therebetween. The first opening is larger than the second opening.

19 Claims, 5 Drawing Sheets

TUBING ATTACHMENT TOOL AND METHODS OF USING SAME

CROSS-REFERENCE TO RELATED APPLICATION

The present application is based on and claims priority to U.S. Provisional Application 61/105,977 having a filing date of Oct. 16, 2008, which is incorporated by reference herein.

BACKGROUND

Various medical devices are designed for implantation into living organisms. These devices often have ports which allow access into and out of the devices. The ports can be connected to tubing material and can provide for, among other things, repeated access to the venous system for the parenteral delivery of medications, fluids, and nutritional solutions and for the sampling of venous blood. In addition, as discussed in U.S. patent application Ser. No. 12/202,664 entitled Arteriovenous Access Valve System and Process, devices can include ports that are utilized to inflate or deflate valves to restrict blood flow such as through an arteriovenous graft.

However, a challenge in utilizing these devices is the difficulty of connecting tubing material with the ports of the devices. In particular, it is often very cumbersome to push tubing material over a port, especially considering the conditions for making such a connection. For example, surgical gloves are typically worn when attempting to connect tubing material with a port, making gripping difficult. In addition, blood and/or other fluids that are present in the area where attachment is likely to occur can make all of the various surfaces slippery and difficult to grasp.

Presently, traditional forceps are typically used when attempting a connection between the tubing material and the port of a medical device. Due to the limited space and accessibility that is often available, utilization of forceps is awkward at best. The problem is exacerbated by the limitation of visibility caused by the requirement of one or both hands being in the work area. Furthermore, significant pressure must be employed to push the tubing material onto the port of a device and when the prongs of the forceps press against the tubing and the port, the tubing can receive damage. Tubing material is typically polyurethane or some similarly elastic material which can be easily damaged by the hard surface of the outlet, which is often a metallic material, and the hard surface of the forceps, which are also typically metallic material. When tubing material is damaged, the tubing material must be re-cut, adding both time and frustration to the procedure.

The problems and difficulties suggested are not intended to be exhaustive, but rather are among many which may tend to reduce the effectiveness of prior medical forceps. However, in view of the above, a need currently exists in the art for a tubing attachment tool that can prevent damage to tubing and minimize time required for connection to the port of a device. A method for using such a tool is also needed.

SUMMARY

In general, the present disclosure is directed to a tubing attachment tool. The tubing attachment tool includes first and second frames pivotally joined to one another such that the first and second frames can pivot to an open position and a closed position. Each of the first and second frames have a first handle end and a second end distal to the first handle end with each second end including a tubing grasping element. Each tubing grasping element includes a first curved surface and a second curved surface. When the first and second frames are in a closed position the first curved surfaces of the tubing grasping elements are aligned adjacent to one another and the second curved surfaces of the tubing grasping elements are aligned adjacent to one another such that the first curved surfaces define a first opening capable of housing an open end of tubing for attachment and the second curved surfaces define a second opening capable of grasping a portion of tubing inserted therebetween. The first opening is larger than the second opening.

In accordance with still another embodiment of the present disclosure, a method for attaching tubing is described. The method includes providing a tubing attachment tool. The tubing attachment tool includes first and second frames pivotally joined to one another such that the first and second frames can pivot to an open position and a closed position. Each of the first and second frames have a first handle end and a second end distal to the first handle end with each second end including a tubing grasping element. Each tubing grasping element includes a first generally semi-circular surface and a second generally semi-circular surface. When the first and second frames are in a closed position the first generally semi-circular surfaces of the tubing grasping elements are aligned adjacent to one another and the second generally semi-circular surfaces of the tubing grasping elements are aligned adjacent to one another such that the first generally semi-circular surfaces define a first generally circular opening capable of housing an open end of tubing for attachment and the second generally semi-circular surfaces define a second generally circular opening capable of grasping a portion of tubing inserted therebetween. The first generally circular opening is larger than the second generally circular opening. A portion of tubing is grasped with the tubing attachment tool by utilizing the handle ends to move the first and second frames to a closed position such that a portion of tubing is inserted between the grasping elements and an open end of the tubing is housed in the first generally circular opening defined by the first generally semi-circular surfaces. The open end of the tubing is attached to the port of a medical device.

Other features and aspects of the present invention are discussed in greater detail below.

BRIEF DESCRIPTION OF THE DRAWINGS

A full and enabling disclosure of the present invention is set forth in the specification with reference to the following figures.

Figure 1A:
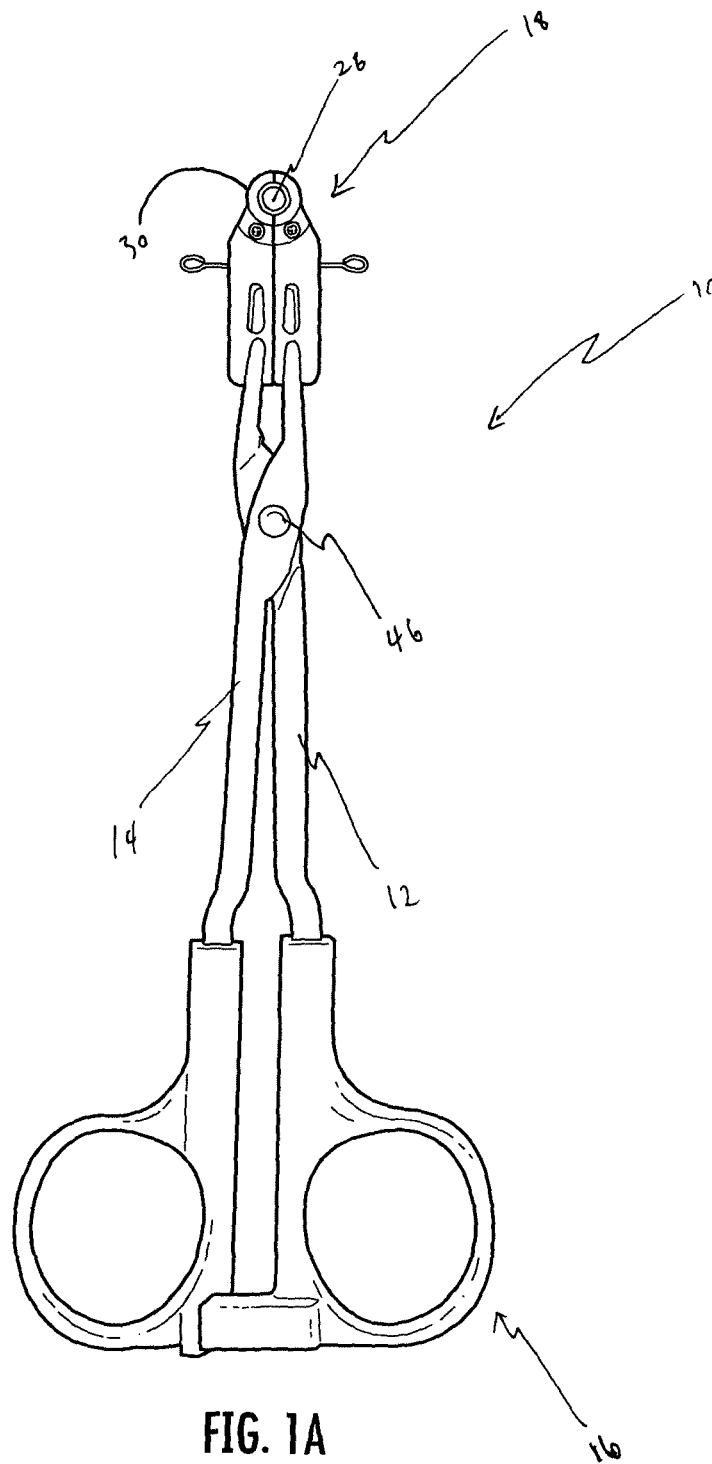
FIGS. 1A and 1B illustrate a device in accordance with one embodiment of the present disclosure.

Repeat use of reference characters in the present specification and drawings is intended to represent the same or analogous features of the invention.

DETAILED DESCRIPTION

Reference now will be made to the embodiments of the invention, one or more examples of which are set forth below. Each example is provided by way of explanation of the invention, not as a limitation of the invention. In fact, it will be apparent to those skilled in the art that various modifications and variations may be made in the invention without departing from the scope or spirit of the invention. For instance, features illustrated or described as part of one embodiment may be used in another embodiment to yield a still further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied in the exemplary construction.

In general, the present disclosure is directed to a tubing attachment tool. The tubing attachment tool of the present disclosure can assist in more easily connecting tubing to the port of a medical device. Specifically, the tool is designed to reduce the likelihood of damage to tubing material while the tubing material is being connected to a port. Furthermore, the tool is relatively inexpensive to manufacture and is also intuitive to use.

Figure 1B:
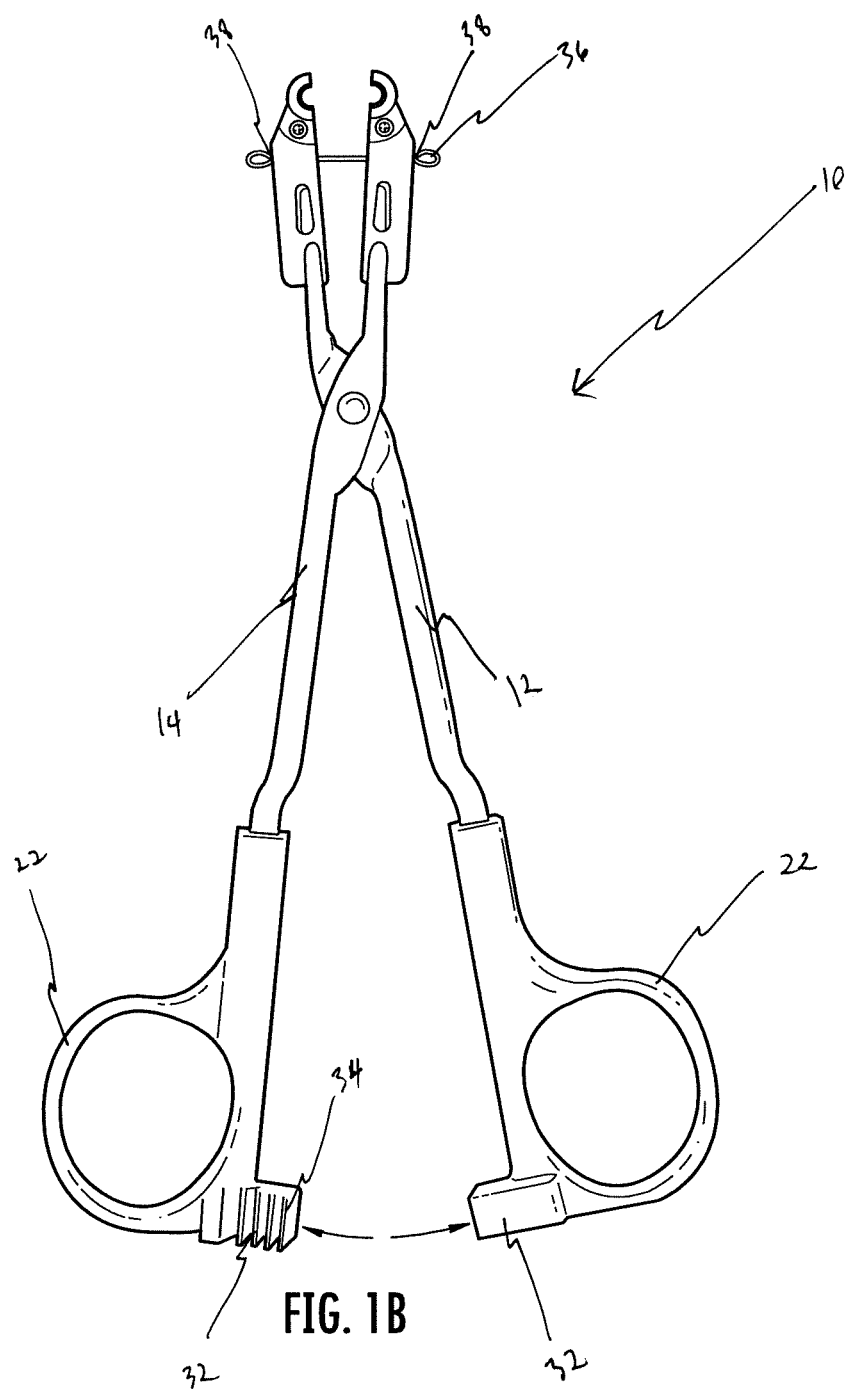
Figure 1C:
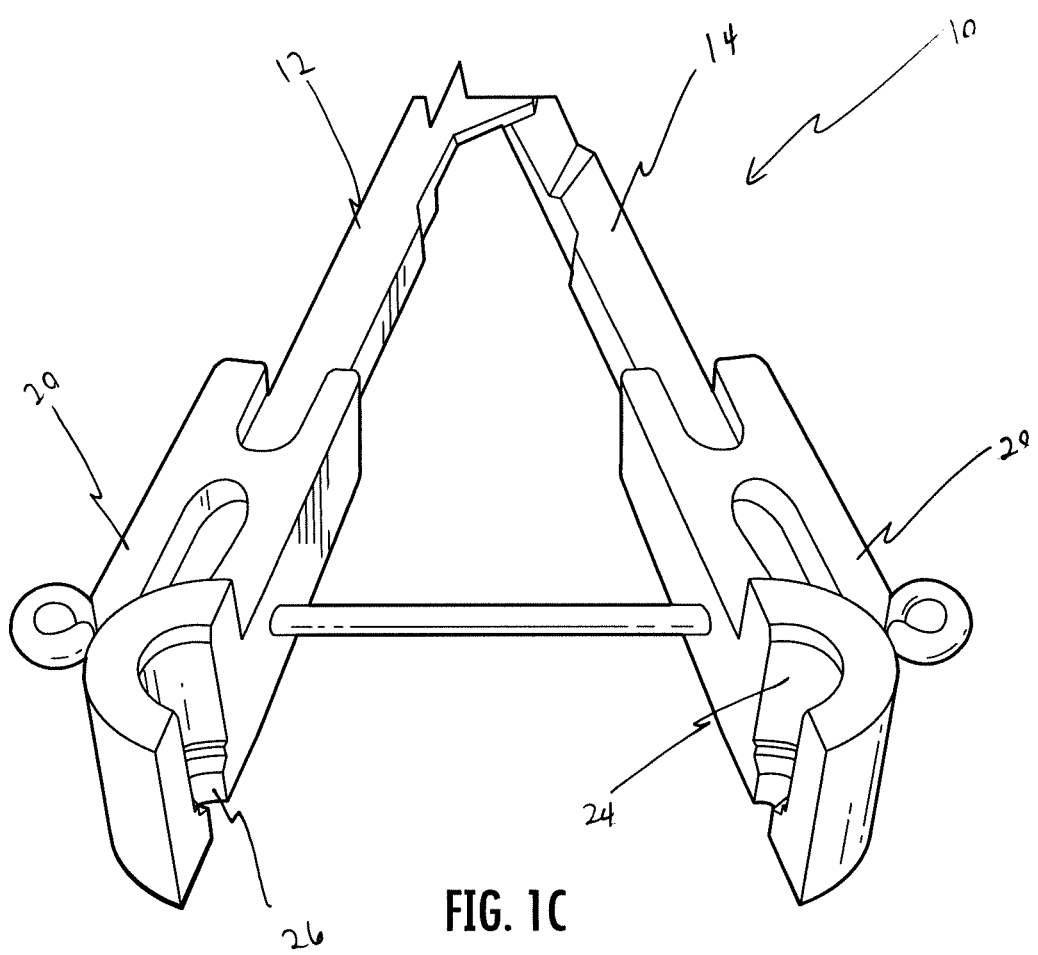
FIG. 1C is a perspective view of a portion of device in accordance with one embodiment of the present disclosure.

Turning to FIG. 1A, a tubing attachment tool 10 in accordance with one embodiment of the present disclosure is illustrated. The tubing attachment tool 10 includes first frame 12 and second frame 14. The frames 12, 14 can be made of any suitable material such as metal, plastic, or the like. The frames 12, 14 can also include an antibacterial coating or can be formed from a material having antibacterial properties. The frames 12, 14 each include a first handle end 16 and a second end 18 that is distal to the first handle end 16. The frames 12, 14 are joined together so as to allow the frames to pivot to an open position and a closed position. The frames 12, 14 can be joined together at a pivot point 46 as would be known and understood to one of ordinary skill in the art to allow them to pivot from a closed position to an open position and vice versa. In this regard, a closed position can include when the second ends 18 of frames 12, 14 are in contact with one another, as illustrated in FIG. 1A. However, it should be understood that a closed position can also include other positions such as when the second ends of frames 12, 14 are not in contact with one another, but are close enough together to grasp tubing therebetween (as will be explained in greater detail below). Referring to FIG. 1B, the tubing attachment tool 10 is shown in an open position.

Tubing attachment tool 10 can include a locking mechanism 32 which can assist in maintaining tool 10 in a closed position. Locking mechanism 32 includes one or more teeth 34 on each frame 12, 14. The teeth 34 are shaped to intermesh with one another so as to hold the tool 10 in a closed position. In this manner, a user can easily maintain the tool 10 in a closed position. The locking mechanism can be included as part of the first handle end 16 of frames 12, 14. Once locked, the teeth 34 can be separated by urging a tooth 34 out of the plane of the corresponding tooth 34, such as by adjusting handle end 16 of frames 12, 14. It should be understood, however, that any suitable locking mechanism can be utilized with the present disclosure on any suitable portion of the tubing attachment tool 10.

Tubing attachment tool 10 can also include a restrictor element 36. The restrictor element 36 can limit the range of pivot between frames 12, 14 so as to prevent the frames from opening too widely in the open position. As illustrated, frames 12, 14 each define a restrictor element opening 38 with the restrictor element 36 having a length extending through each opening 38 so as to restrict the frames from pivoting beyond the length of the restrictor element to an open position while still allowing the frames to pivot freely within the length defined by the restrictor element. In certain embodiments, the restrictor element can have a length of from about 1 mm to about 20 mm, in particular a length from about 1 mm to about 10 mm, and still more particularly a length from about 1 mm to about 5 mm.

As shown in FIGS. 1A and 1B, the frames 12, 14 each include a first handle end 16 and a second end 18 that is distal to the first handle end 16. The first handle end 16 is designed to allow a user to move the frames 12, 14 between an open position and closed position. For instance, the first handle end 16 can include a circular shaped handle 22 that can receive one or more fingers of a user. However, it should be understood that first handle end 16 can be of any suitable shape and size as would be understood in the art.

Turning to FIG. 2C, second end 18 of frames 12, 14 includes a tubing grasping element 20. The tubing grasping element 20 can be formed from the same material as the frame to which it is joined. Tubing grasping element 20 can be integrally connected to frame 12, 14. In addition, tubing grasping element 20 can be formed from one or more different materials from frames 12, 14 and can be attached to frames 12, 14 using any suitable method as would be known in the art.

Each tubing grasping element 20 includes a first curved surface 24 and a second curved surface 26. Each curved surface can also define a length. For instance, one or both of the first curved surface 24 and second curved surface 26 can be generally semi-circular. Similarly, if one or both of the first curved surface 24 and second curved surface 26 are generally semi-circular, the semi-circular surface(s) can define a length that is generally semi-cylindrical. The first curved surface 24 can have a larger width and length than the second curved surface 26.

As illustrated in FIG. 1A, the first and second curved surfaces 24, 26 of frame 12 define a first opening 28 and second opening 30 when paired with first and second curved surfaces 24, 26, respectively, of frame 14. Again, first opening 28 can have a larger width and length than second opening 30. In addition, in embodiments when one or both curved surfaces 24, 26 of each frame 12, 14 have a generally semi-circular shape, one or both of the first opening 28 or second opening 30 defined by the surfaces can have a generally circular shape and can define a length that is generally cylindrical. However, it should be understood that the curved surfaces 24, 26 can have any suitable curved shape so long as the paired first curved surfaces are capable of receiving tubing and the paired second curved surfaces are capable of grasping tubing as discussed in more detail below.

For example, in embodiments where a generally circular opening is defined by paired semi-circular surfaces 24, the opening can have a diameter from about 0.05 mm to about 10 mm, more specifically a diameter of from about 0.5 mm to about 7 mm, and still more specifically a diameter of from about 0.5 mm to about 2 mm.

Figure 2A:
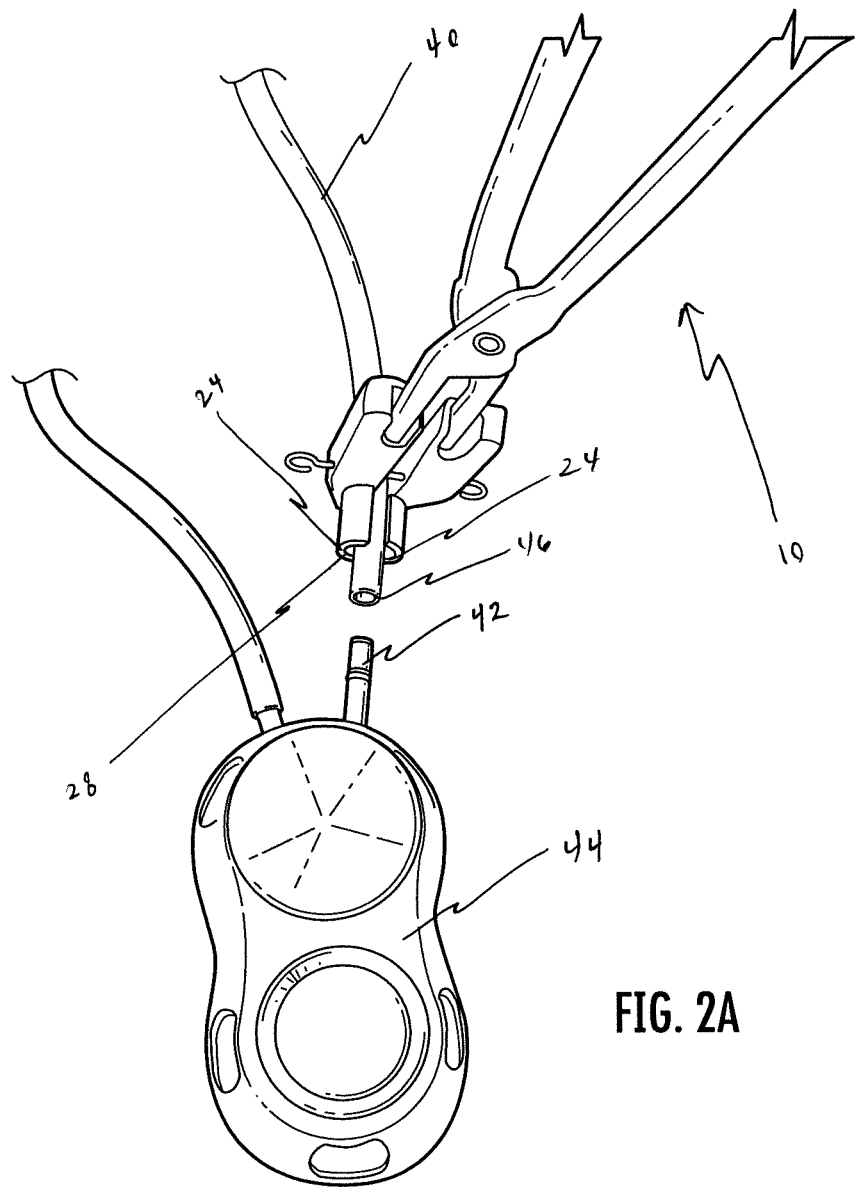
FIGS. 2A and 2B are perspective views of a method of using a device in accordance with one embodiment of the present disclosure.

Turning to FIG. 2A, a method for attaching tubing is provided. A tubing attachment tool 10 as described herein can be utilized to grasp a portion of tubing 40 and attach it to the port 42 of a medical device 44. An example of one such medical device can be found in U.S. patent application Ser. No. 12/202,664 entitled Arteriovenous Access Valve System and Process, which is incorporated by reference herein. However, any medical device having a port to which tubing is attached is contemplated for use with the present disclosure. Tubing can refer to any tubing as would be known in the art such as polyurethane tubing or a similarly flexible tubing material. In addition, the tubing attachment tool described herein can be utilized to attach tubing to any medical device as would be understood in the art and can be used with both in vivo and ex vivo procedures.

Figure 2B:
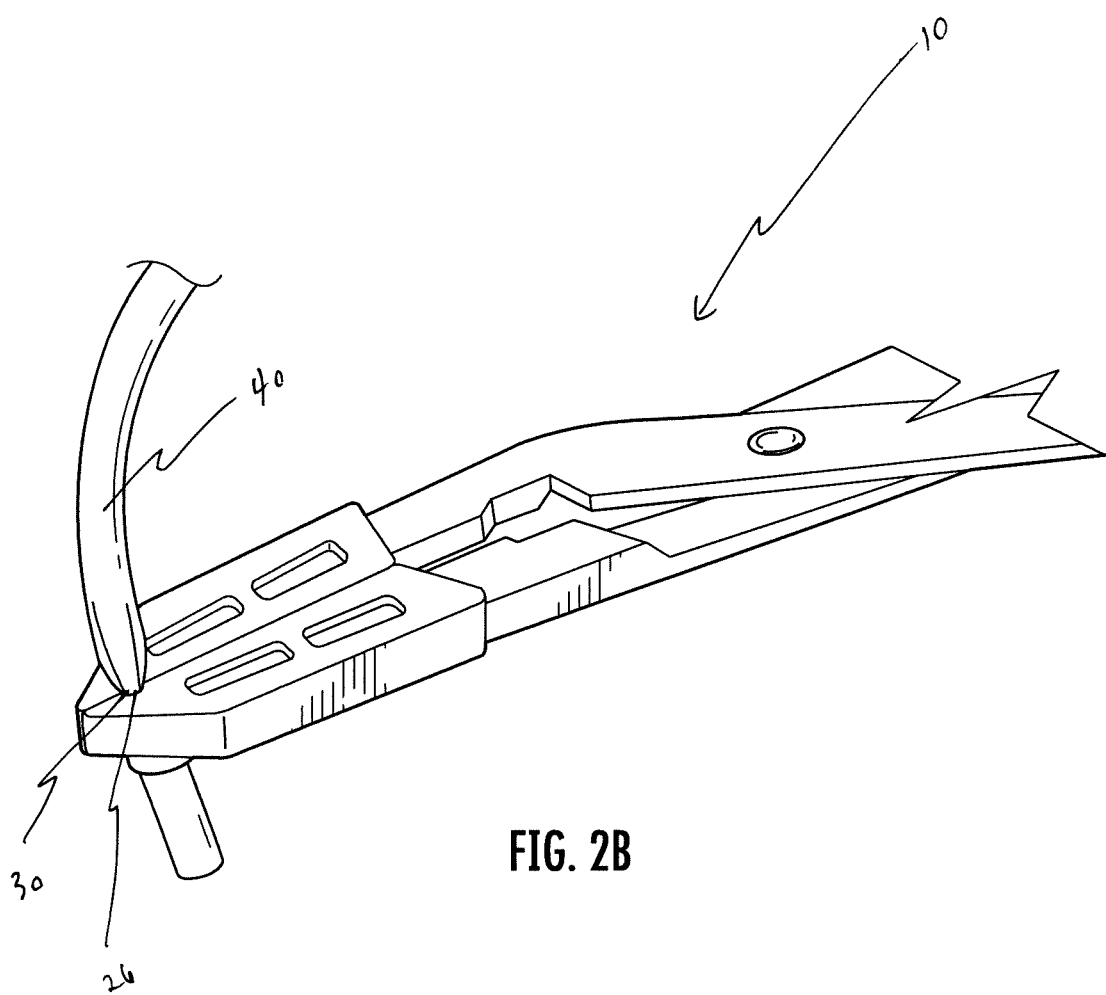

A user can hold tubing attachment tool 10 by the first handle end 16 of frames 12, 14 (as shown in FIG. 1A, such as with circular shaped handle 22) in order to pivot the frames 12, 14 from an open position to a closed position after locating tubing 40 between tubing grasping elements 20. In particular, as shown in FIG. 2B, the smaller opening 30 defined by second curved surfaces 26 is able to grasp tubing 40 without puncturing or damaging the tubing. The curved surfaces 26 can ensure even application of pressure against the tubing. In certain embodiments, for example, the curved surfaces 26 can have a generally semi-circular shape and define an opening that is generally circular. Second curved surfaces 26 can also define a length that can assist in grasping tubing. In certain embodiments, the length can be generally semi-cylindrical in shape.

Turning again to FIG. 2A, an open end 46 of tubing 40 is housed within the opening 28 defined by first curved surfaces 24 and, as illustrated, extends partially from opening 28. In this manner, tool 10 can be used to place tubing over the port 42 of a device 44. As the tubing 40 is placed over port 42, opening 28 can provide space for the port 42 to move into the opening so as to not require readjustment of the tool 10 as the tubing is being attached. Indeed, one or both of the first curved surface 24 can be generally semi-circular (as illustrated) and can define a length that is generally semi-cylindrical which allows the opening to be complimentary to the shape of the tubing 40 over the port 42. In this manner, the tubing can be attached to the port without causing damage to the tubing.

Once the tubing is attached to the port, a locking lure (not illustrated) can be positioned over the portion of the tubing that is attached to the port to help prevent the tubing from coming disattached. In this regard, the tool described herein can also be utilized to slide the locking lure in place over the tubing and port.

The tool as described herein is designed to reduce the likelihood of damage to tubing material while the tubing material is being connected to a port. It is also contemplated that the tool be relatively inexpensive to manufacture and intuitive to use.

In the interests of brevity and conciseness, any ranges of values set forth in this specification are to be construed as written description support for claims reciting any sub-ranges having endpoints which are whole number values within the specified range in question. By way of a hypothetical illustrative example, a disclosure in this specification of a range of 1-5 shall be considered to support claims to any of the following sub-ranges: 1-4; 1-3; 1-2; 2-5; 2-4; 2-3; 3-5; 3-4; and 4-5.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A tubing attachment tool comprising:
   first and second frames pivotally joined to one another such that the first and second frames can pivot to an open position and a closed position wherein the first and second frame each define an opening with a single restrictor element having a length extending through each opening such that the first and second frames are restricted from pivoting beyond the length of the restrictor element to an open position, each of the first and second frames having a first handle end and a second end distal to the first handle end, each second end comprising a tubing grasping element, each tubing grasping element comprising a first generally curved surface and a second generally curved surface, wherein when the first and second frames are in a closed position the first generally curved surfaces of the tubing grasping elements are aligned adjacent to one another and the second generally curved surfaces of the tubing grasping elements are aligned adjacent to one another such that the first generally curved surfaces define an opening capable of housing an open end of tubing for attachment and the second generally curved surfaces define a second opening capable of grasping a portion of tubing inserted therebetween, the first opening being larger than the second opening.

2. A tool as in claim 1, wherein the first generally curved surfaces are generally semi-circular in shape.

3. A tool as in claim 2, wherein the opening defined by the first generally curved surfaces is generally circular in shape.

4. A tool as in claim 1, wherein the second generally curved surfaces are generally semi-circular in shape.

5. A tool as in claim 1, wherein the restrictor element has a length of from about 1 mm to about 20 mm.

6. A tool as in claim 1, further comprising a locking mechanism, the locking mechanism comprising one or more teeth on both the first and second frames, the one or more teeth from the first frame being configured to intermesh with the one or more teeth from the second frame so as to hold the first and second frames in a closed position.

7. A tool as in claim 6, wherein the locking mechanism is present on the handle ends of the first and second frames.

8. A tool as in claim 1, wherein the tubing grasping elements are integrally joined to the first and second frames.

9. A tool as in claim 1, wherein the handle ends are generally circular in shape.

10. A method for attaching tubing, comprising:
    providing a tubing attachment tool, the tubing attachment tool comprising first and second frames pivotally joined to one another such that the first and second frames can pivot to an open position and a closed position, each of the first and second frames having a first handle end and a second end distal to the first handle end, each second end comprising a tubing grasping element, each tubing grasping element comprising a first generally semi-circular surface and a second generally semi-circular surface, wherein when the first and second frames are in a closed position the first generally semi-circular surfaces of the tubing grasping elements are aligned adjacent to one another and the second generally semi-circular surfaces of the tubing grasping elements are aligned adjacent to one another such that the first generally semi-circular surfaces define a first generally circular opening capable of housing an open end of tubing for attachment and the second generally semi-circular surfaces define a second generally circular opening capable of grasping a portion of tubing inserted therebetween, the first generally circular opening being larger than the second generally circular opening;
    grasping a portion of tubing with the tubing attachment tool by utilizing the handle ends to move the first and second frames to a closed position such that a portion of tubing is inserted between the grasping elements and an open end of the tubing is housed in the first generally circular opening defined by the first generally semi-circular surfaces;

attaching the open end of the tubing to the port of a medical device.

11. A method as in claim 10, wherein the first generally circular opening defined by the first generally semi-circular surfaces has a diameter of from about 0.05 mm to about 10 mm.

12. A method as in claim 10, wherein the second generally circular opening defined by the second generally semi-circular surfaces has a diameter of from about 0.5 mm to about 10 mm.

13. A method as in claim 10, wherein the first generally circular opening defined by the first generally semi-circular surfaces has a diameter of from about 0.5 mm to about 2 mm.

14. A method as in claim 10, wherein the first and second frame each define an opening with a single restrictor element having a length extending through each opening such that the first and second frames are restricted from pivoting beyond the length of the restrictor element to an open position.

15. A method as in claim 14, wherein the tubing grasping elements are from about 1 mm to about 7 mm apart when the first and second frames are in an open position.

16. A method as in claim 10, further comprising a locking mechanism, the locking mechanism comprising one or more teeth on both the first and second frames, the one or more teeth from the first frame being configured to intermesh with the one or more teeth from the second frame so as to hold the first and second frames in a closed position.

17. A method as in claim 16, wherein the locking mechanism is present on the handle ends of the first and second frames.

18. A method as in claim 10, wherein the tubing grasping elements are integrally joined to the first and second frames.

19. A method as in claim 10, wherein the handle ends are generally circular in shape.

* * * * *